(12) United States Patent
Saha et al.

(10) Patent No.: US 7,358,072 B2
(45) Date of Patent: Apr. 15, 2008

(54) FERMENTATIVE PRODUCTION OF MANNITOL

(75) Inventors: Badal Saha, Peoria, IL (US); Francis Michael Racine, Peoria, IL (US); Elena Terentieva, Moscow (RU)

(73) Assignees: ZuChem, Inc, Chicago, IL (US); The United States of America as represented by the Secretary of Agriculture, Washington, DC (US)

( * ) Notice: Subject to any disclaimer, the term of this patent is extended or adjusted under 35 U.S.C. 154(b) by 224 days.

(21) Appl. No.: 11/250,671

(22) Filed: Oct. 14, 2005

(65) Prior Publication Data

US 2006/0134765 A1   Jun. 22, 2006

Related U.S. Application Data

(60) Provisional application No. 60/619,488, filed on Oct. 15, 2004.

(51) Int. Cl.
   *C12P 7/18*   (2006.01)
(52) U.S. Cl. ..................................... 435/158
(58) Field of Classification Search ................ 435/158
   See application file for complete search history.

(56) References Cited

U.S. PATENT DOCUMENTS 6,602,691 B1   8/2003   Ojamo et al. ............... 435/158
6,855,526 B2   2/2005   Saha .......................... 435/158

FOREIGN PATENT DOCUMENTS

EP   0486024   5/1992
WO   0250296   6/2002

OTHER PUBLICATIONS

Guimaraes, et al., "Fermentation of Sweet Whey by Ethanologenic Escherichia coli", Biotechnology and Bioengineering, vol. 40, pp. 41-45 (1992).
Grohmann, et al., "Fermentation of Orange Peel Hydrolysates by Ethanologenic Escherichia coli", Applied Biochemistry and Biotechnology, vol. 57/58, p. 383-388 (1996).
Soetaert, "Production of Mannitol with Leuconostoc mesenteroides", Med. Fac. Landbouww, Rijksuniv. Gent. 55/4, p. 1549-1552, 1990.
Notification of Transmittal the International Search Report and Written Opinion for PCT/US2005/036947 dated Feb. 14, 2006.
Soetaert, et al., "Production of D-mannitol and D-lactic acid by fermentation with Leuconostoc mesenteroides", Argo-Food Industry Hi-Tech, 6:41-44, 1995.
von Weymarn, et al., "Scale-up of a New Bacterial Mannitol Production Process", Biotechnol, Prog. 2003, 19, 815-821.
von Weymarn, et al., "High-level production of D-mannitol with membrane cell-recycle bioreactor", Journal of Industrial Microbiology & Biotechnology, (2002) 29, 44-49.
Debord, et al., "Study of Different Crystalline Forms of Mannitol: Comparative Behaviour Under Compression", Drug. Dev. Ind. Pharm., 13:1533-1546, 1987.
Makkee, et al., "Production Methods of D-Mannitol", Starch/Starke, 37 (1985) Nr. 4, S. 136-141.
Vandamme, et al., "Biotechnical modification of carbohydrates", FEMS Microbiology Reviews, 16 (1995) 163-186.
Yun, et al., "Microbial Transformation of Fructose to Mannitol by Lactobacillus SP. KY-107", Biotechnology Letters, vol. 18, No. 1, (1996) pp. 35-40.
Yun, et al., "A Comparative Study of Mannitol Production by Two Lactic Acid Bacteria", Journal of Fermentation and Bioengineering, vol. 85, No. 2, 203-208, 1998.
Korakli, et al., "Production of mannitol by Lactobacillus sanfranciscensis", Adv. Food Sci.(CMTL). vol. 22, No. 1/2, 1-4 (2000).
Saha, et al., "Production of Mannitol and Lactic Acid by Fermentation with Lactobacillus intermedius NRRL B-3693", Biotechnology & Bioengineering, vol. 82, No. 7, 2003, p. 866-887.
Wisselink, et al., "Mannitol production by lactic acid bacteria: a review". Int. Dairy Journal, 12 (2002) 151-161.
Chang, et al., "High Density Cell Culture by Membrane-Based Cell Recycle", Biotech. Adv., vol. 12, p. 467-487, 1994.
Bothast, et al. "Fermentation of L-Arabinose, D-Xylose and D-Glucose by Ethanologenic Recombinant Klebsiella Oxytoca Strain P2", Biotechnology Letters, vol. 16, No. 4, pp. 401-406 (1994).

*Primary Examiner*—Herbert J Lilling
(74) *Attorney, Agent, or Firm*—McDonnell Boehnen Hulbert & Berghoff LLP

(57) ABSTRACT

The invention provides processes for continuous fed-batch fermentative production and continuous recycle fermentative production of mannitol.

31 Claims, 6 Drawing Sheets

Fermenter Broth

Hollow Fiber Microfiltration:
500 kDa MWCO

Ultrafiltration
10 kDa MWCO

Charcoal treatment, 75 C;
Charcoal removal by pressure filtration

Cooling and crystallization

Crystal collection and washing in a basket centrifuge

Dry crystals under vacuum at 50-55°C

FERMENTATIVE PRODUCTION OF MANNITOL

PRIORITY

This application claims the benefit of U.S. Ser. No. 60/619,488, filed Oct. 15, 2004.

BACKGROUND OF THE INVENTION

Mannitol, a naturally occurring polyol, is widely used in the food, pharmaceutical, medicine and chemical industries (Soetaert et al., Agro Food Ind. Hi-Tech. 6:41-44, 1995). It is used as a sweet-tasting bodying and texturing agent. Mannitol reduces the crystallization tendency of sugars and is used as such to increase the shelf-life of foodstuffs. Crystalline mannitol exhibits a very low hygroscopicity, making it useful in products that are stable at high humidity. It is extensively used in chewing gum. Because of its desirable properties, mannitol is commonly used in the pharmaceutical formulation of chewable tablets and granulated powders. It prevents moisture absorption from the air, exhibits excellent mechanical compressing properties, does not interact with the active components, and its sweet cool taste masks the unpleasant taste of many drugs (Debord et al., Drug Dev. Ind. Pharm. 13:1533-1546, 1987). The complex of boric acid with mannitol is used in the production of dry electrolytic capacitors. It is an extensively used polyol for production of resins and surfactants. Mannitol is used in medicine as a powerful osmotic diuretic and in many types of surgery for the prevention of kidney failure and to reduce dye and brain oedema. Mannitol hexanitrate is a well known vasodilator, used in the treatment of hypertension.

Mannitol is currently produced industrially by high pressure hydrogenation of fructose/glucose mixtures in aqueous solution at high temperature (120-160°) with Raney nickel as catalyst. Typically, the hydrogenation of a 50/50 fructose/glucose mixture results in an approximately 30/70 mixture of mannitol and sorbitol (Makkee et al., Starch/Starke 37:136-141, 1985). Therefore about half of the fructose is converted to mannitol and half of it to sorbitol. The glucose is hydrogenated exclusively to sorbitol. As a consequence, the commercial production of mannitol is always accompanied by the production of sorbitol, thus reducing the conversion efficiency of substrate to mannitol (Soetaert et al., 1995, supra).

In recent years, research efforts have been directed towards production of polyols by fermentation and enzymatic means (Vandamme et al. FEMS Microbiol. Rev. 16:163-186, 1995). Yun et al., (Biotechnol. Letts. 18:35-40, 1996) describe microbial transformation of fructose to mannitol by *Lactobacillus* sp. KY-107. In shake flask cultures, Yun obtained a final concentration of 70 g mannitol/L from 100 g D-fructose within 80 h at 28° C. Yun et al. (J. Ferment. Bioeng. 85:203-208, 1998) report the isolation of two mannitol-producing, lactic acid bacteria from kimichi, a traditional Korean food. *Lactobaccilus* sp. Y-107 transformed fructose to mannitol from the early growth stage, with a 54% conversion yield after 20 h; whereas *Leuconostoc* sp. Y-002 converted fructose to mannitol more slowly with a 40% yield at 20 h. Yun et al. (1998, supra) describe the pathway for microbial mannitol formation as comprising two mechanisms. In the first mechanism, NADPH-linked mannitol dehydrogenase directs the reduction of fructose. In the second mechanism, fructose-6-phosphate is initially reduced to mannitol-1-phosphate by means of NAD(P)H-linked mannitol-1-phosphate dehydrogenase. The mannitol-1-phosphate is then converted to inorganic phosphate and mannitol by means of a specific mannitol-1-phosphatase.

Korakli et al. (Adv. Food Sci. (CTML) 22:1-4, 2000) describe the production of mannitol in a fermentation process with selected strains of *Lactobacillus sanfranciscensis* with the ability to utilize maltose, sucrose and glucose as carbon sources. Cells of strain LTH 2590 were adapted to sucrose, but gave a decreased yield of mannitol production in relation to the fructose content of sucrose.

Itoh et al. (European Patent Number EP0486024, 1992) teaches the use of *Lactobacillus* sp. B001 (FERM BP-3158) for the production of mannitol, acetic acid and lactic acid on carbohydrate substrates comprising glucose and fructose. Itoh et al. reports obtaining a level of 12.3% mannitol in 23 h with a yield of sugar of 61%. Though being able of use other sugars, such as glucose, galactose, maltose and xylose, strain B001 does not metabolize mannose or trehalose.

Methods are needed in the art to increase volumetric productivity and mannitol concentration in fermentative production of mannitol.

SUMMARY OF THE INVENTION

One embodiment of the invention provides an improved process for continuous fed-batch fermentative production of mannitol. The process comprises culturing a microorganism capable of producing mannitol in a fermentation broth under conditions suitable to produce mannitol. The improvement comprises using a fermentation broth having corn steep liquor as a complex nitrogen source and about 0.2 ml/L to about 1 ml/L protease. The fermentation broth can also comprise about 0.01 g/L to about 0.2 g/L tryptophan, 0.5 g/L to about 20 g/L casein hydrolysate, about 0.01 g/L to about 0.2 g/L tyrosine, about 0.01 g/L to about 0.2 g/L aspartic acid, or combinations thereof. The pH of the fermentation broth can be about 5.0 to about 6.0 during fermentation. The production of mannitol can be greater than about 150 g/L. The rate of production of mannitol can be greater than about 6 g/L-h. The microorganism(s) can be *Lactobacillus intermedius, Leuconostoc mesenteroides* subsp. *dextranicum, Lactobacillus cellobiosus, Leuconostoc paramesenteroides, Lactobacillus fermentum, Lactobacillus buchneri, Leuconostoc amelibiosum, Lactobacillus brevis, Lactobacillus citrovorum* or a combination thereof. The pH can be controlled with $NH_4OH$, NaOH, gaseous $NH_3$, $CaCO_3$, or combinations thereof. The process can further comprise clearing the fermentation broth by centrifugation, filtration or hollow fiber filtration. The filtration can comprise adding $CaCO_3$ to the fermentation broth and lowering the pH with sulfuric acid and filtering the fermentation broth. The process can further comprise concentrating the fermentation broth to about 30% to 36% mannitol by batch evaporation or continuous flow evaporation. The process can further comprise crystallizing the concentrated fermentation broth. The fermentation broth can comprise about 64 g/L initial volume to about 120 g/L initial volume of corn steep liquor.

Another embodiment of the invention provides an improved process for continuous recycle fermentative production of mannitol. The process comprises culturing a microorganism capable of producing mannitol in a fermentation broth under conditions suitable to produce mannitol. The improvement comprises using fermentation broth having corn steep liquor as a complex nitrogen source and about 0.2 ml/L to about 1 ml/L protease. The fermentation broth can further comprise about 0.01 g/L to about 0.2 g/L tryptophan, about 0.5 g/L to about 20 g/L casein hydrolysate, about 0.2 g/L tyrosine, about 0.01 g/L to about 0.2 g/L aspartic acid, or a combination thereof. The pH of the fermentation broth can be about 5.0 to about 6.0 during fermentation. A dilution range can be about 0.1 to about 0.55 vol/h. The rate of production of mannitol can be greater than about 30 g/L-h. The microorganism can be *Lactobacillus intermedius, Leuconostoc mesenteroides* subsp. *dextranicum, Lactobacillus cellobiosus, Leuconostoc paramesenteroides, Lactobacillus fermentum, Lactobacillus buchneri, Leuconostoc amelibiosum, Lactobacillus brevis, Lactobacillus citrovorum* or a combination thereof. The pH can be controlled with $NH_4OH$, NaOH, gaseous $NH_3$, $CaCO_3$, or a combination thereof. The process can further comprise clearing the fermentation broth by centrifugation, filtration or hollow fiber filtration. The filtration can comprise adding $CaCO_3$ to the fermentation broth and lowering the pH with sulfuric acid and filtering the fermentation broth. The process can further comprise concentrating the fermentation broth to about 30% to 36% mannitol by batch evaporation or continuous flow evaporation. The concentrated fermentation broth can be crystallized. The initial substrate concentrations can be about 9% to about 15% fructose and from about 2% to about 10% glucose. The fermentation broth can comprise about 10 to about 40 g/L corn steep liquor.

Therefore, the invention provides high accumulation of mannitol at high volumetric productivities in a continuous fed-batch process. The production of more than 160 g/L mannitol while maintaining a rate of more than 7 g/L-h is unprecedented for a fed-batch process. The high final mannitol concentration is particularly unique to this invention and will reduce the amount of evaporation needed in recovery and thereby reduces costs. Additionally, the invention provides high volumetric productivity in a continuous recycle process. Production rates up to 40 g/L-h can be achieved in, e.g., a membrane recycle reactor.

The use of high fructose corn syrup and corn steep liquor will reduce production cost relative to other described processes that use expensive yeast extracts, protein hydrolysates and pure fructose and glucose. The continuous process uses a very low concentration of nutrients and the medium is very economical.

The fermentation processes produce no other polyols and the mannitol is easily purified in a few simple steps. This is a big advantage over the hydrogenation process, which requires removal of the catalyst and a difficult separation of sorbitol and mannitol. The high final concentration of mannitol in the fed-batch process has the advantage of making the evaporation step less costly. In the continuous process the lower steep level reduces impurities and makes recovery of a pure product less expensive and easier.

DETAILED DESCRIPTION OF THE INVENTION

Figure 1:
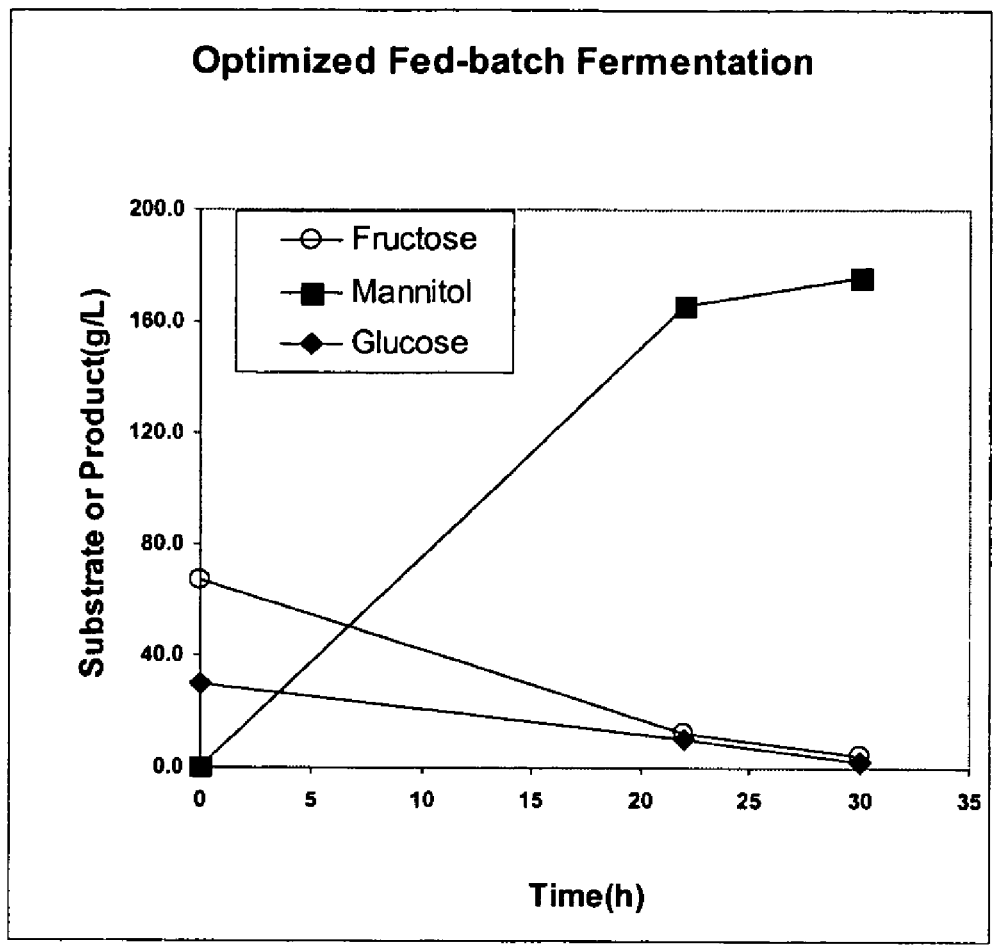
FIG. 1 shows an optimized continuously fed-batch process. Closed squares: mannitol; open squares: fructose; Closed diamonds: glucose.

In one embodiment of the invention mannitol is produced via continuous fed-batch fermentation. Continuous fed-batch processes use the addition of nutrients throughout the fermentation. Broth is removed from the fermenter at the same rate that nutrients are added, so that a constant volume in the tank is maintained. Continuous fed-batch fermentations can be maintained for e.g., two weeks, a month or longer.

Another embodiment of the invention provides for continuous recycle fermentative production of mannitol. Cell recycling can increase mannitol productivity by operating at a higher steady-state cell concentration compared to a system without cell recycle. Where cell recycle is used, a portion of the fermenter contents is withdrawn from the fermenter, the microorganisms in the portion are concentrated and are returned to the fermenter. The concentration can be done by, e.g., microfiltration or centrifugation. The growth of microorganisms depends on the dilution rate. The dilution rate can be, for example, from about 0.1 to about 0.55 fermenter volumes per hour.

Fermentation Medium

The primary carbon source for use in the methods of the invention is fructose, which may also be used as the sole carbon source. Secondary carbon sources can be used in combination with fructose and include, e.g., glucose, maltose, mannose, raffinose, trehalose, and galactose, without limitation thereto. Starch can also be used as a secondary carbon source, provided that glucoamylase is introduced into the fermentation medium to promote saccharification during the course of the fermentation. The amount of secondary carbon source can be up to about 33% (w/w) of the total substrate. A preferred secondary carbon source is glucose.

In fed-batch processes, based on initial volume, corn steep liquor concentrations can be from about 64 to about 120 g/L; fructose concentration can be from about 240 to about 300 g/L and glucose concentration can be from about 120 to about 150 g/L. A continuous feed solution for a recycle fermenter can contain, for example, corn steep liquor concentration of about 10 to about 40 g/L; fructose concentration of about 100 to about 125 g/L and glucose concentration of about 50 to about 62 g/L. This can be fed at, for example, about 0.1 to about 0.5 fermenter volumes per hour.

The specific fermentation medium for use in the mannitol production, other than corn steep liquor and protease, is not necessarily critical, and selection thereof would be within the skill of an ordinary person in the art. A suitable medium contains sources of protein, amino acids, salts and other growth stimulating components. One media is simplified MRS medium [10 g peptone, 5 g yeast extract, 2 g ammonium citrate, 5 g sodium acetate, 0.1 g magnesium sulfate, 0.05 g manganese sulfate and 2 g disodium phosphate per liter (final pH 6.5)] and enriched MRS medium (same as the simplified medium but additionally containing 10 g beef extract and 1.0 ml TWEEN™ 80). Sodium acetate can be omitted from the simplified MRS medium. MRS medium, however is too expensive for commercial manufacturing. Therefore, the salts, peptone, and yeast extract can be replaced with corn steep liquor, a by-product of the corn wet-milling industry.

Fermentations can be conducted by combining the carbon source with the medium in any suitable fermenter, and inoculating with a suitable microorganism. Initial levels of carbon substrate should not exceed about 120 g/L, and should preferably be about 60 to about 100 g/L. Additional substrate is added during the fermentation to reach about 360 to about 450 g per liter of initial volume. The fermentation is carried out either aerobically or anaerobically under conditions conducive to the growth of the microorganism and production of mannitol dehydrogenase. Fermentation temperature should be maintained within the range of at least about 25° C., and less than about 50° C. Preferably, the temperature is at least about 30° C. and less than or equal to about 37° C. Peak mannitol levels occur shortly after the organism completes its log phase growth, typically within about 24-96 hours post-inoculation. At higher levels of initial carbon substrate, longer periods of fermentation are of course required to maximize mannitol production.

Amino Acids and Proteases

About 0.01 g/L to about 0.2 g/L tryptophan can be added to the fermentation broth. Other additions include, e.g., about 0.5 g/L to about 20 g/L casein hydrolysate; about 0.5 g/L to about 20 g/L casein hydrolysate and about 0.01 g/L and about 0.2 g/L tryptophan; about 0.5 g/L to about 20 g/L soy peptone; about 0.5 g/L to about 20 g/L yeast extract; about 0.01 g/L to about 0.2 g/L tryptophan, about 0.01 g/L to about 0.20 g/L tyrosine, and about 0.01 g/L to about 0.2 g/L aspartic acid. Furthermore, about 0.2 mL per liter to about 1 mL per liter protease can be added to the fermentation broth. Any protease that hydrolyzes proteins to amino acids at a pH of about 6 to about 3 can be used.

Microorganisms

Microorganisms can be, e.g., *Lactobacillus intermedius* (e.g., strain NRRL B-30560), *L. intermedius* NRRL B-3693, *Leuconostoc mesenteroides* subsp. *dextranicum*, *Lactobacillus cellobiosus*, *Leuconostoc paramesenteroides*, *Lactobacillus fermentum*, *Lactobacillus buchneri*, *Leuconostoc amelibiosum*, *Lactobacillus brevis*, *Lactobacillus citrovorum* or a combination thereof.

pH and pH Control

The pH of the fermentation medium at the beginning of the fermentation is typically within the range of about 6-7, and then is controlled by addition of base at about pH 4.5 to about 6.0, preferably from about 5.0 to about 5.5 as the fermentation progresses. $NH_4OH$, $NaOH$, and/or gaseous $NH_3$ can be used to control the pH.

Calcium carbonate can also be used as a pH control agent in fermentation. It has the advantage that it can be added to the fermenter before sterilization and does not require automatic pH control equipment. Also, it can be converted to $CaSO_4$ by addition of sulfuric acid and as such can act as a filter aid for clarification of the product and can be used to remove more than 95% of solids (as A660) from the medium.

Clarification of Fermentation Broth

Once fermentation is complete, the fermentation broth can be clarified of cells and debris. Centrifugation or filtration, e.g., hollow fiber filtration, vacuum filtration, microfiltration, or ultrafiltration can be used. Where filtration is used clear supernatant can be further treated with charcoal at concentrations of, e.g., about 0.1, 0.5, 1, 2, 5% or more g/vol for, e.g., 0.5-2 hours with stirring at about 25° C. to about 75° C. The charcoal can be removed by vacuum filtration. To ease filtration, diatomaceous earth can be used as a filter aid at, e.g., 0.1, 0.5, 1, 2, 5% or more g/vol). Other methods know in the art can also be used for cell separation or clarification.

Concentration of Fermentation Broth

The clarified fermentation broth can be concentrated using, e.g., evaporation methods such as batch evaporation or continuous flow evaporation (thin or rolling film). Preferably, clarified fermentation broth is concentrated to about 32-34% (w/v) prior to crystallization step. If mannitol is under-concentrated, there will be too much left in the broth after crystallization, which leads to lower yield, even when the mother-liquor is recycled, since each new recycle step will accumulate more impurities. If mannitol is over-concentrated, the thick slurry of crystals will interfere with the separation and wash. Also, at concentrations higher than about 37-38% the crystallization is too rapid to control. If over-concentration does occur, the broth should be diluted to the appropriate level before crystallization starts.

Crystallization and Recovery of Mannitol

Upon completion of the fermentation, mannitol can be recovered from the culture using techniques conventional in the art. For example, when mannitol is present in the culture broth at levels exceeding the solubility limit (180 g/L at 25° C.), it can be recovered from solution by cooling crystallization.

Figure 5:
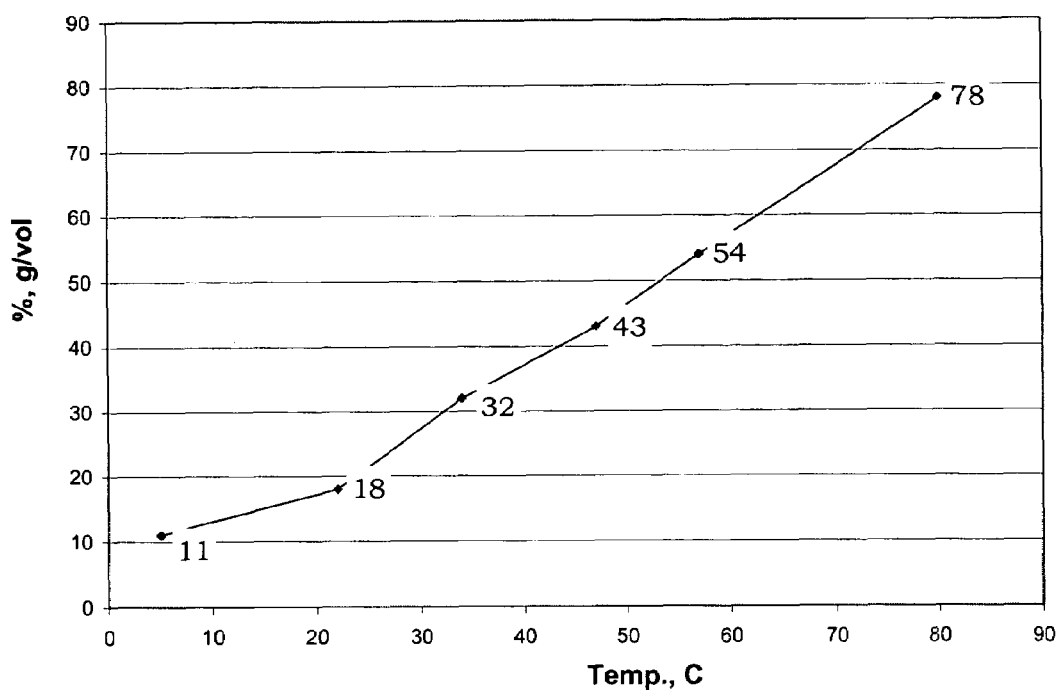
FIG. 5 shows a mannitol saturation curve.

The highest recovery of crystals can be achieved when mannitol is concentrated to about 32-34%, but acceptable results can be obtained with concentrations up to about 37-38% when proper care is taken. FIG. 5 shows a saturation curve of a mannitol solution. When precipitating the product from the broth it is necessary to remember that the solution has many additional components that may have caramelized during the hot charcoal treatment and evaporation steps. This can increase viscosity and create special ionic interactions in the broth, and thus influence the process of mannitol crystallization.

In practice, mannitol can be crystallized from the crude fermentation broth by chilling the crude broth to about 4° C. Separation and washing of mannitol crystals from the solution can be done with a number of devices, such as a perforated basket centrifuge, a Buchner funnel, vacuum filtration, or a Nutche-filter. After mannitol recovery, lactic acid and acetic acid can be easily recovered from the fermentation broth by electrodialysis.

In continuous fed-batch processes of the invention mannitol concentrations of about 166 g/L can be achieved in about 22 hours. This rate, 7.5 g/L-h, is unprecedented for such a high concentration of mannitol. In continuous recycle processes of the invention, volumetric productivities as high as 40 g/L-h can be achieved.

All patents, patent applications, and other scientific or technical writings referred to anywhere herein are incorporated by reference in their entirety. The methods and compositions described herein as presently representative of preferred embodiments are exemplary and are not intended as limitations on the scope of the invention. Changes therein and other uses will be evident to those skilled in the art, and are encompassed within the spirit of the invention. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Effect of pH Control on the Production of Mannitol by *Lactobacillus intermedius* NRRL B-3693

The fermentation protocol of (Bothast et al., Biotechnol. Lett. 16:401-406(1994)) with 150 g/L fructose was used to determine the effect of controlling pH at various levels. In these fermentations the initial pH was 6.5 but fell rapidly to the indicated control points and was maintained there with NaOH. Mannitol production occurred over a fairly broad pH range, from 4.5-6.0, with the optimum rate at pH 5.0-5.5. The percent conversion of fructose to mannitol and the relative proportions of mannitol, lactic acid and acetic acid produced were similar at each pH tested.

TABLE I

Effect of pH control on the production of mannitol from fructose by *Lactobacillus intermedius* NRRL B-3693

| pH controlled at | Time (h) | Unutilized substrate (g/L) | Mannitol yield (g/L) | Lactic Acid yield (g/L) | Acetic Acid yield (g/L) |
|---|---|---|---|---|---|
| 4.5 | 23 | 9.6 ± 7.3 | 96.7 ± 4.9 | 22.5 ± 1.7 | 15.7 ± 0.1 |
| 5.0 | 23 | 0.0 ± 0.0 | 105.7 ± 0.0 | 23.5 ± 1.2 | 16.8 ± 0.2 |
| 5.5 | 23 | 0.0 ± 0.0 | 104.2 ± 1.0 | 24.4 ± 0.5 | 16.8 ± 0.1 |
| 6.0 | 23 | 8.4 ± 8.4 | 102.3 ± 1.1 | 23.9 ± 0.1 | 16.5 ± 0.2 |

TABLE I-continued

Effect of pH control on the production of mannitol from fructose by *Lactobacillus intermedius* NRRL B-3693

| pH controlled at | Time (h) | Unutilized substrate (g/L) | Mannitol yield (g/L) | Lactic Acid yield (g/L) | Acetic Acid yield (g/L) |
|---|---|---|---|---|---|
| 6.5 | 23 | 139.3 ± 0.0 | 7.8 ± 0.1 | 2.2 ± 0.1 | 1.3 ± 0.0 |
| 7.0 | 23 | 141.6 ± 0.5 | 5.4 ± 0.3 | 2.0 ± 0.1 | 1.0 ± 0.0 |

15% fructose in modified MRS medium and initial pH 6.5 with the indicated pH control points.
Values are the average of two fermenters ± the standard deviation.

Example 2

Optimizing Steep and Peptone Concentrations

Modified MRS medium is too expensive for manufacturing, so some typical industrial ingredients were tested. Corn steep liquor (CSL) was tested as a replacement for the salts, yeast extract and peptone. Since CSL is not uniform and the products from some suppliers may not be as productive as others, we tested methods to optimize CSL to yield consistent growth media.

1. CSL Comparison From Different Sources

Mannitol production using CSL from various sources was tested in fleakers as described in Example 1 except that the medium consisted only of CSL and manganese plus about 29% fructose. The fructose was sterilized separately and added to the sterile fleakers. Since the pH of CSL is low the unadjusted pH of the medium was around 4.0 and the initial pH of the sterilized medium was adjusted to 5.0 with NaOH before inoculation. Table II shows the results of the comparison study. When dosed on an equal weight per volume basis, there were clear differences in the rate of mannitol production despite using relatively high concentrations (75 g/L of liquid products and 37.5 g/L dry powders). The rate of production in this simplified medium was faster than that reported for the modified MRS medium at high fructose concentration (Saha, U.S. Pat. No. 6,855,526). Conversion of 300 g/L fructose in modified MRS medium required 136 hours compared to conversion of 272 g/L in 50 hours in this example with CSL.

TABLE II

Corn Steep Liquor Sources

| Media[1] | % Fructose | Hours | Mannitol g/L SD | Lactic acid g/L SD | Acetic acid g/L SD | Mannitol prod. rate g/L/hr | Remaining fructose (g/L) |
|---|---|---|---|---|---|---|---|
| Cargill CSL + Mn | 28.9 | 50.0 | 199.2 ± 42.5 | 63.2 ± 11.2 | 31.9 ± 5.4 | 4.0 | 17.0 |
| GPC CSL + Mn | 29.3 | 89.0 | 150.4 ± 0.3 | 56.9 ± 0.3 | 25.7 ± 0.3 | 1.7 | 107.3 |
| Roquette CSL + Mn | 28.7 | 89.0 | 206.0 ± 0.7 | 69.0 ± 1.9 | 33.8 ± 1.2 | 2.3 | 26.6 |
| RoqPowder CSL + Mn | 29.2 | 74.0 | 153.4 ± 9.0 | 52.4 ± 24.0 | 26.0 ± 1.4 | 2.1 | 102.4 |

[1]Media consisted of 0.0033% Manganese sulfate and 7.5% Corn Steep Liquor, except Roquette powder was half this assuming a 50% solids for the Roquette liquid.
Cargill CSL was from Cargill, Blair NE, Roquette CSL was Roquette Solulys K, Keokuk IA and GPC CSL was from Grain Processing Corporation, Muscatine IA.

In order to understand how the different CSL batches gave such a wide range of production rates, they were analyzed for free amino acid composition and the results are shown in Table III. The Solulys K was limited in aspartic acid, glutamine, tryptophan, tyrosine and histidine relative to the Cargill batch. The GPC steep was about 50% lower in all free amino acids, but like Solulys K was completely lacking tryptophan.

TABLE III

Amino Acid Composition of Some Corn Steep Liquors

| | Steep Source | | | | |
|---|---|---|---|---|---|
| | Cargill | GPC | | Roquette solulys K | |
| | ug AA/ mg sample | ug AA/ mg sample | % of Cargill | ug AA/ mg sample | % of Cargill |
| L-Aspartic acid | 3.40 | 1.93 | 56.7% | 0.39 | 11.6% |
| L-Threonine | 2.40 | 1.23 | 51.2% | 2.42 | 100.7% |
| L-Serine | 3.07 | 1.59 | 51.8% | 3.11 | 101.4% |
| L-Asparagine | 3.77 | 1.84 | 48.7% | 2.60 | 69.1% |
| L-Glutamic acid | 5.45 | 2.44 | 44.8% | 4.49 | 82.5% |
| L-Glutamine | 1.05 | 0.60 | 56.7% | 0.04 | 3.4% |
| L-Proline | 9.16 | 4.76 | 52.0% | 7.37 | 80.5% |
| L-Glycine | 1.59 | 0.83 | 52.3% | 1.70 | 107.1% |
| L-Alanine | 7.12 | 3.57 | 50.2% | 8.52 | 119.6% |
| L-Valine | 4.48 | 2.37 | 52.9% | 4.35 | 97.2% |
| L-Cystine | 0.17 | 0.14 | 80.8% | 0.28 | 162.2% |
| L-Methionine | 2.29 | 1.24 | 54.1% | 2.39 | 104.3% |
| L-Isoleucine | 2.22 | 1.30 | 58.3% | 2.63 | 118.2% |
| L-Leucine | 9.65 | 5.15 | 53.4% | 8.84 | 91.7% |
| L-Tyrosine | 3.07 | 1.72 | 55.9% | 0.00 | 0.0% |
| L-Phenylalanine | 4.63 | 2.41 | 52.1% | 3.73 | 80.6% |
| Ethanolamine | 0.16 | 0.09 | 58.7% | 0.24 | 150.2% |
| L-Tryptophan | 0.37 | 0.00 | 0.0% | 0.00 | 0.0% |
| Ammonia | 0.60 | 0.39 | 64.6% | 0.63 | 104.4% |
| L-Ornithine | 0.34 | 0.19 | 56.7% | 0.83 | 245.4% |
| L-Lysine | 4.22 | 2.27 | 53.8% | 3.54 | 83.8% |
| L-Histidine | 1.66 | 0.84 | 50.8% | 0.04 | 2.2% |
| L-Arginine | 6.34 | 3.15 | 49.7% | 5.16 | 81.5% |
| TOTAL | 77.21 | 40.06 | 51.9% | 63.31 | 82.0% |

Free amino acid analysis was performed by: Scientific Research Consortium, Inc., 1769 Lexington Avenue North, Suite #321, St. Paul, MN 55113

2. Enhancing Steep Performance

The results reported in Table II demonstrated that certain CSL batches can support higher mannitol production rates and final concentrations than others when used as the sole source of nitrogen and vitamins and other co-factors. We next investigated means to enhance mannitol production with less productive batches of CSL. We also explored the use of supplements to reduce high levels of steep solids in order to make downstream recovery of mannitol cleaner. Some possibilities already demonstrated are soy peptone and yeast extract, components of modified MRS medium (Saha & Nakamura, Biotechnology and Bioengineering 82:866-87, 2003). Although these are too expensive to use as sole nitrogen sources, they could be used at low concentration as supplements to CSL at about 1 to about 10 g/L, and preferably at about 1 to about 2 g/L.

A simplified fermentation protocol was used to screen various nutrients for their ability to enhance mannitol production. A base medium with the "deficient" CSL was prepared in fleakers, with 150 g/L fructose and 0.05 g/L manganese sulfate. A seed culture was grown in 100 mL of modified MRS medium in a 250 mL flask for 8 hours at 37 C, 130 RPM. Table IV A and B show the results of screening tests. As seen in Table IVA, the productivity of the basal medium was enhanced about 50% by a 2.5-fold increase in the concentration of the same steep liquor, but this was only half the increase obtained by the addition of a similar amount of another steep, from Cargill, or by the addition of a soy peptone. A yeast extract stimulated 60% as much as the soy peptone at the same concentration. A mixture of salts equivalent to MRS medium showed minimal stimulation. Further tests (Table IVB) showed that another peptone, Nutricepts HSP-A was also effective. While hydrolyzed casein (vitamin free) with cysteine could not substitute effectively for peptone, we also discovered that hydrolyzed casein plus tryptophan could. These results show that tryptophan is an important nutrient for this process and that other components of hydrolyzed casein were also important.

TABLE IV

Supplementing CSL

A. Supplementing Solulys K CSL with different nutrients

| Addition | g/L | Initial g/L Fructose | Hours | Mannitol g/L SD | Mannitol prod. rate g/L/hr |
|---|---|---|---|---|---|
| None | 0 | 150 | 13.5 | 28.4 ± 0.2 | 2.1 |
| Solulys K steep | 75(125 total) | 150 | 13.5 | 41.0 ± 1.1 | 3.0 |
| Cargill steep | 75(125 total) | 150 | 13.5 | 91.8 ± 2.5 | 6.8 |
| Marcor Soy Peptone D | 10 | 150 | 13.5 | 90.3 ± 0.4 | 6.7 |
| MRS salts | same as MRS | 150 | 13.5 | 31.1 ± 2.8 | 2.3 |

B. Supplementing Solulys K CSL with different peptones

| Addition | g/L | Initial g/L Fructose | Time Hours | Mannitol g/L ± SD | Mannitol prod. rate g/L/hr |
|---|---|---|---|---|---|
| Marcor Soy Peptone D | 5 | 150 | 16 | 71.55 ± 4.45 | 4.47 |
| HSP-A Soy Peptone | 5 | 150 | 16 | 84.60 ± 3.82 | 5.29 |
| Cargill steep | 25 | 150 | 15 | 95.7 ± * | 6.38 |

TABLE IV-continued

| | Supplementing CSL | | | | |
|---|---|---|---|---|---|
| Casein hydrolysate + tryptophan | 5 0.166 | 150 | 15 | 100.35 ± 1.38 | 6.69 |
| Casein hydrolysate + cysteine | 5 0.166 | 150 | 15 | 18.3 ± 0.08 | 1.22 |

Base medium consisted of Roquette Solulys K, 50 g/L; manganese sulfate, 0.05 g/L; fructose, 150 g/L
Fleakers were incubated at 37 C., 130 RPM, pH 5.0
Values are averages of duplicate fleakers with standard (SD) of replicates
Casein hydrolysate was "Vitamin Free Casein Hydrolysate from ICN BioMedicals

3. Standardizing CSL Productivity

The results indicated that these components can be added to improve the performance of different steeps on a custom basis. The general applicability of these results to fermentations with any steep was tested in fleakers. Three steep liquors were tested using the same methods as Tables IV A and B. The steep level was only 3%, a limiting concentration under these conditions even for the best steep liquors. Each steep was tested with tryptophan or with tryptophan plus casein hydrolysate. The results are shown in Table V.

Cargill steep was clearly the best when tested alone and it was only slightly improved by tryptophan, but showed a 42% increase in mannitol production with casein hydrolysate. The Roquette steep showed a 50% increase with tryptophan and casein hydrolysate compared to tryptophan alone. The GPC steep showed very poor results at this concentration, but tryptophan caused a three-fold increase in mannitol and amino acids with tryptophan caused another 50% increase. These results highlight the importance of amino acids and tryptophan in particular in the production of mannitol by *L. intermedius* B3693. However, tryptophan by itself is not able to stimulate mannitol production as well as casein hydrolysate plus tryptophan.

A final set of experiments was performed to confirm the contribution of each amino acid to the performance of the CSL. Some other individual amino acids were tested for their ability to compliment tryptophan. Preliminary results suggested a mixture of trp, tyr, and asp might replace casein hydrolyzate (CH). In these experiments (Table VI) trp and tyr were required for maximum mannitol yield, but asp was not. Using these results it is possible to custom blend a growth media that takes into account the cost of each component and the mannitol productivity desired depending on the source of the CSL and the physical location of the production facility.

TABLE V

Standardizing CSL productivity
Casein hydrolysates and tryptophan

| Steep | Addition | Initial g/L Fructose | Hours | Mannitol g/L | Rate g/L/hr |
|---|---|---|---|---|---|
| 3% Cargill steep | None | 200 | 19 | 81.9 | 4.3 |
| 3% Cargill steep | Trp | 200 | 19 | 87.9 | 4.6 |
| 3% Cargill steep | CH, Trp | 200 | 19 | 116.1 | 6.1 |
| 3% RoquetteSolulys K | Trp | 200 | 19 | 54.0 | 2.8 |
| 3% RoquetteSolulys K | CH, Trp | 200 | 19 | 78.9 | 4.2 |
| 3% Grain Processing steep | none | 200 | 19 | 15.6 | 0.8 |
| 3% Grain Processing steep | Trp | 200 | 19 | 45.6 | 2.4 |
| 3% Grain Processing steep | CH, Trp | 200 | 19 | 69.0 | 3.6 |

Base medium consisted of manganese sulfate, 0.05 g/L; fructose, 200 g/L
Casein hydrolysate (CH) was "Vitamin Free Casein Hydrolysate" from ICN BioMedicals
L-Tryptophan (trp) was from Sigma; CH was added at 5 g/L and Trp was 0.33 g/L

TABLE VI

Standardizing CSL productivity
Tryptophan, tyrosine, aspartic acid

| Steep | Addition | g/L | Initial g/L Fructose | Hours | Mannitol g/L ± SD | Mannitol prod. rate g/L/hr |
|---|---|---|---|---|---|---|
| 5% | Trp, tyr, asp | 0.167 each | 150 | 13 | 72.3 ± 1.7 | 5.6 |
| 5% | Omit asp | 0.167 each | 150 | 13 | 69.3 ± 2.97 | 5.3 |
| 5% | Omit tyr | 0.167 each | 150 | 13 | 49.5 ± 7.42 | 3.8 |
| 5% | Omit trp | 0.167 each | 150 | 13 | 40.2 ± 2.97 | 3.1 |

TABLE VI-continued

Standardizing CSL productivity
Tryptophan, tyrosine, aspartic acid

| Steep Addition | g/L | Initial g/L Fructose | Hours | Mannitol g/L ± SD | Mannitol prod. rate g/L/hr |
|---|---|---|---|---|---|
| 3% Trp, tyr, asp | 0.167 each | 150 | 13 | 62.7 ± 1.48 | 4.8 |
| 2% Trp, tyr, asp | 0.167 each | 150 | 13 | 53.7 ± 2.33 | 4.1 |

Base medium consisted of Solulys K, 50 g/L; manganese sulfate, 0.05 g/L; fructose, 150 g/L
Fleakers were incubated at 37 C., 130 RPM, pH 5.0
Values are averages of duplicate fleakers with standard (SD) of replicates
L-Tryptophan (trp), L-tyrosine (tyr) and L-aspartic acid (asp) were from Sigma

Example 3

Use of Protease to Stimulate Mannitol Production by *Lactobacillus intermedius* NRRL B-3693.

As shown in Example 2, free amino acids appear to be critical to the production of mannitol. Therefore, protease addition to the fermentation was tested with various steeps. Table VII shows a comparison of the effect of protease on mannitol production with three different steeps. The procedure of example 2, Table VII was used with corn steep liquors, 50 g/L, manganese sulfate, 0.05 g/L, glucose, 70 g/L and fructose 130 g/L. Glucose was added based on the observation that up to one-third of the fructose can be replaced with glucose without reducing the yield of mannitol (Saha & Nakamura, Biotechnology and Bioengineering 82:866-87, 2003. Filter sterilized GC106 protease (Genencor International) was added (0.1 mL) to the fermenters and they were incubated for one hour after which the 30 mL inoculum was added. The results in Table VII showed that protease treatment increased the mannitol production rate by varying amounts depending on the source of the steep. A relatively early sample time (15 hours) was chosen to emphasize the effect on the initial rate of the process. The Cargill steep had the highest mannitol of the fermentations without enzyme and showed the least increase with enzyme, 16%. The GPC steep, in contrast, had a very slow rate without enzyme but showed a 230% increase when treated. These results agree with the free amino acid analysis that showed that the GPC steep had the lowest level of free amino acids of these three. The Solulys K was intermediate with a 40% increase.

TABLE VII

A comparison of the effect of protease treatment on mannitol production with 3 different steeps

| Steep Source | g/L | enzyme %* | Time Hours | Mannitol g/L | Mannitol production rate g/L/hr | % increase with enzyme |
|---|---|---|---|---|---|---|
| Cargill | 50 | 0 | 15 | 95.1 | 6.34 | |
| Cargill | 50 | 0.66 | 15 | 110.1 | 7.34 | 15.8% |
| GPC | 50 | 0 | 15 | 16.8 | 1.12 | |
| GPC | 50 | 0.66 | 15 | 55.5 | 3.7 | 230.4% |
| Solulys K | 50 | 0 | 15 | 50.1 | 3.34 | |
| Solulys K | 50 | 0.66 | 15 | 70.2 | 4.68 | 40.1% |

*Enzyme dosage is expressed as mL of enzyme/g of steep × 100

Example 4

Other Strains

Many strains of lactobacilli can convert fructose to mannitol (Wisselink et al., Mannitol production by lactic acid bacteria: a review. *Int Dairy J* 12: 151-161(2002). Using a medium optimized for B3693, with steep and yeast extract, we compared some other known mannitol producers (U.S. Pat. No. 6,855,526). Table VIIIA shows the results of this comparison after 24 hour of fermentation.

TABLE VIII A

Comparison of mannitol production by various lactobacilli using a steepwater and yeast extract medium

| NRRL Strain no. B- | Organism | Mannitol Production Rate, g/L-h* |
|---|---|---|
| 3693 | *Lactobacillus intermedius* | 4.5 |
| 1120 | *Leuconostoc mesenteroides* subsp."*dextranicum*" | 4.0 |
| 1840 | *Lactobacillus cellobiosus* | 3.8 |
| 3471 | *Leuconostoc paramesenteroides* | 3.3 |
| 1915 | *Lactobacillus fermentum* | 3.3 |
| 1860 | *Lactobacillus buchneri* | 3.2 |
| 742 | *Leuconostoc amelibiosum* | 2.8 |
| 1836 | *Lactobacillus brevis* | 0.8 |
| 1147 | *Lactobacillus citrovorum* | 0.5 |

Medium: Cargill steep, 60 g/L, Manganous sulfate, 0.05 g/L, Expressa 2200 yeast extract, 2 g/L; 70 g/L glucose and 140 g/L fructose;
*Rate based on 24 h fermentation at 32 C.

The fermentation temperature was 32° C. for this comparison because some of the strains, especially the *Leuconostoc* species, did not grow well at 37° C. Strain B-3693 was again the best, although slower at 32° C. than at 37° C.

The strain in Table VIIIA were also tested on steep that was less productive for B-3693, and lower productivity was found for all of them than on Cargill steep. Medium optimization procedures as described for *Lactobacillus intermedius* NRRL B-3693 were applied to two other strains, *Lactobacillus cellobiosus* NRRL B-1840 and *Leuconostoc amelibiosum* NRRL B-742 and significant improvements were found. Table VIIIB and C show some results.

*Lactobacillus cellobiosus* B-1840 responded to various complex nitrogen sources in a manner similar to *L. intermedius*. The best level of production was obtained with Cargill steep supplemented with yeast extract. In this case, protease gave no further increase. Solulys K alone gave a much lower yield. Supplementation with yeast plus protease raised the yield almost to the level of Cargill steep plus yeast.

TABLE VIII B

Medium optimization for mannitol production by *Lactobacillus cellobiosus* B-1840

| Nitrogen source | Mannitol Production Rate, g/L-h* |
|---|---|
| Cargill steep | 3.2 |
| Cargill steep + yeast extract | 4.1 |
| Cargill steep + yeast extract + protease | 4.1 |
| Solulys K | 1.5 |
| Solulys K + yeast extract | 3.3 |
| Solulys K + yeast extract + protease | 3.8 |

All fleakers contained manganous sulfate, 0.05 g/L; fructose 140 g/l and glucose 70 g/L.
Nitrogen sources and protease where indicated were: Steep, 60 g/L; Yeast extract Expressa 2200, 1 g/L; protease GC106, 0.3 mL/L;
*Rate based on 24 h fermentation, 37 C.

TABLE VIIIC

Medium optimization for mannitol production by *Leuconostoc amelibiosum* NRRL B-742

| Nitrogen source | Mannitol Production Rate, g/L-h* |
|---|---|
| Cargill steep + yeast extract | 3.3 |
| Solulys K | 0.57 |
| Solulys K + soy peptone | 2.49 |
| Solulys K + CH + Trp | 2.49 |

All fleakers contained manganous sulfate, 0.05 g/L; fructose 140 g/l and glucose 70 g/L.
Nitrogen sources and protease where indicated were: Steep, 60 g/L; Soy peptone Marcor D, 5 g/L; Casein hydrolysate(CH, ICN vitamin free), 5 g/L; L-tryptophan(Trp), 0.2 g/L;
*Rate based on 23 h fermentation, 32 C.

Soy peptone and casein hydrolysate plus tryptophan both significantly stimulated mannitol production by *Leuconostoc amelibiosum* NRRL B-742. Although they were clearly stimulated by the medium enhancements neither *Lactobacillus cellobiosus* NRRL B-1840 nor *Leuconostoc amelibiosum* NRRL B-742 reached the productivity level of *Lactobacillus intermedius* NRRL B-3693 at 37° C.

These results emphasize that mannitol production by other strains can be stimulated by the methods described here. Inexpensive CSL can be a productive nutrient when the proper supplementation and/or protease treatment is applied. However, *Lactobacillus intermedius* NRRL B-3693 under the optimized conditions described had the best combination of fast production rate and high mannitol concentration.

Example 5

Mannitol Production by *Lactobacillus Intermedius* NRRL B-3693; $NH_4$ Versus NaOH for pH Control Many production facilities use $NH_3$ or $NH_4OH$ for pH control rather than NaOH. $NH_3$ can be a nutrient for many processes, but it can also inhibit others, A set of fleakers was run with either 5N $NH_4OH$ or 5N NaOH, added on demand to control pH at 5.0 to see what the effect would be on mannitol production. Seeds and fleakers were prepared as described in Example 2 with 15% fructose, 7.5% steep and 0.05% manganese sulfate. The pH was adjusted with either 5N NaOH or 5N $NH_4OH$ (62 mL of concentrated $NH_4OH$ diluted with deionized water to 100 mL). The fleakers were adjusted to pH 5.0 after sterilization and cooling, prior to inoculation, and then controlled at pH 5.0 with the same reagent after inoculation. A pair of fleakers was run with each control agent.

The results were typical for fleakers with NaOH control. The average mannitol production for the two control fleakers at 10.5 hours was 79.8 g/L and the average with $NH_4OH$ was 82.8 g/L.

Therefore, using $NH_4OH$ results in the same high productivity as seen with NaOH. Gaseous $NH_3$ should also work, keeping in mind that if $NH_3$ is used there would not be the 7-8% dilution that we see now with aqueous additions.

TABLE IX

A comparison of ammonium hydroxide and sodium hydroxide for pH control

| pH Control Agent | Time (h) | Mannitol g/L | Mannitol Production Rate g/L-h |
|---|---|---|---|
| NaOH | 10.5 | 79.8 ± 0.42 | 7.60 |
| $NH_4OH$ | 10.5 | 82.8 ± 0.0 | 7.88 |

Example 6

Optimized Fed Batch Fermentation Process for Mannitol Production by *Lactobacillus intermedius* NRRL B-3693

Saha & Nakamura (2003) showed that a discontinuous fed-batch process could reduce the long lags seen when high substrates levels were used. To further optimize the process, a continuous feed at various feed rates of fructose and glucose was examined. The process is further improved by incorporating the medium optimizations taught in Examples 2 and 3. A B. Braun Biostat®B fermenter was used. The initial medium contained 112 g corn steep liquor (50% solids), 0.08 g manganese sulfate monohydrate, and 3.5 g soy peptone (HSP-A from Nutricepts) in 830 mL, sterilized in the fermenter at 121° C. for 15 min and 67 g fructose plus 34 g glucose in 120 mL sterilized separately and added to the fermenter when cooled. Then protease was added (0.4 mL of GC106), the temperature was adjusted to 37° C., the pH was adjusted to 5.0 with 5 N NaOH. A seed culture was prepared as in example 2 and 50 mL of seed was added to the fermenter. Additional substrate consisting of 228 g fructose and 106 g glucose was added in 400 mL at a rate of 22 mL per hour. Mannitol and fructose were monitored by HPLC. See, FIG. 1. A mannitol concentration of 166 g/L was achieved in 22 hours. This rate, 7.5 g/L-h, is unprecedented for such a high concentration of mannitol.

This fermentation process, in addition to being very productive is relatively simple and economical. Because the organism does not require oxygen, no aeration is required and mixing is minimal. Therefore, the cost of operating the fermenter is lower than processes requiring oxygen. Also, without aeration and agitation of the broth the fermenter can be filled to a greater percentage of gross capacity. Finally, little heat is generated and minimal cooling is required, further reducing costs.

Example 7

Optimized Cell Recycle Fermentation for Mannitol Production by *Lactobacillus intermedius* NRRL B-3693

The process shown in Example 6 is the most productive fed-batch process for mannitol. An alternative with even higher volumetric productivities is a continuous recycle fermentation, using microfiltration membranes to retain cells in the fermenter while continuously feeding substrate and removing product in the permeate. This mode of operation is known to yield higher cell densities and correspondingly higher productivities than traditional fermenters when the organism and process are tolerant of this mode of operation. Chang et al., Biotechnology Advances 12:467-487 (1994).

We have established that *Lactobacillus intermedius* B-3693 performs very well in such a system and we have optimized the conditions for mannitol production, leading to volumetric productivities as high as 40 g/L-h. This example shows a range of variables that can be used in this process and their effect on productivity.

Figure 2:
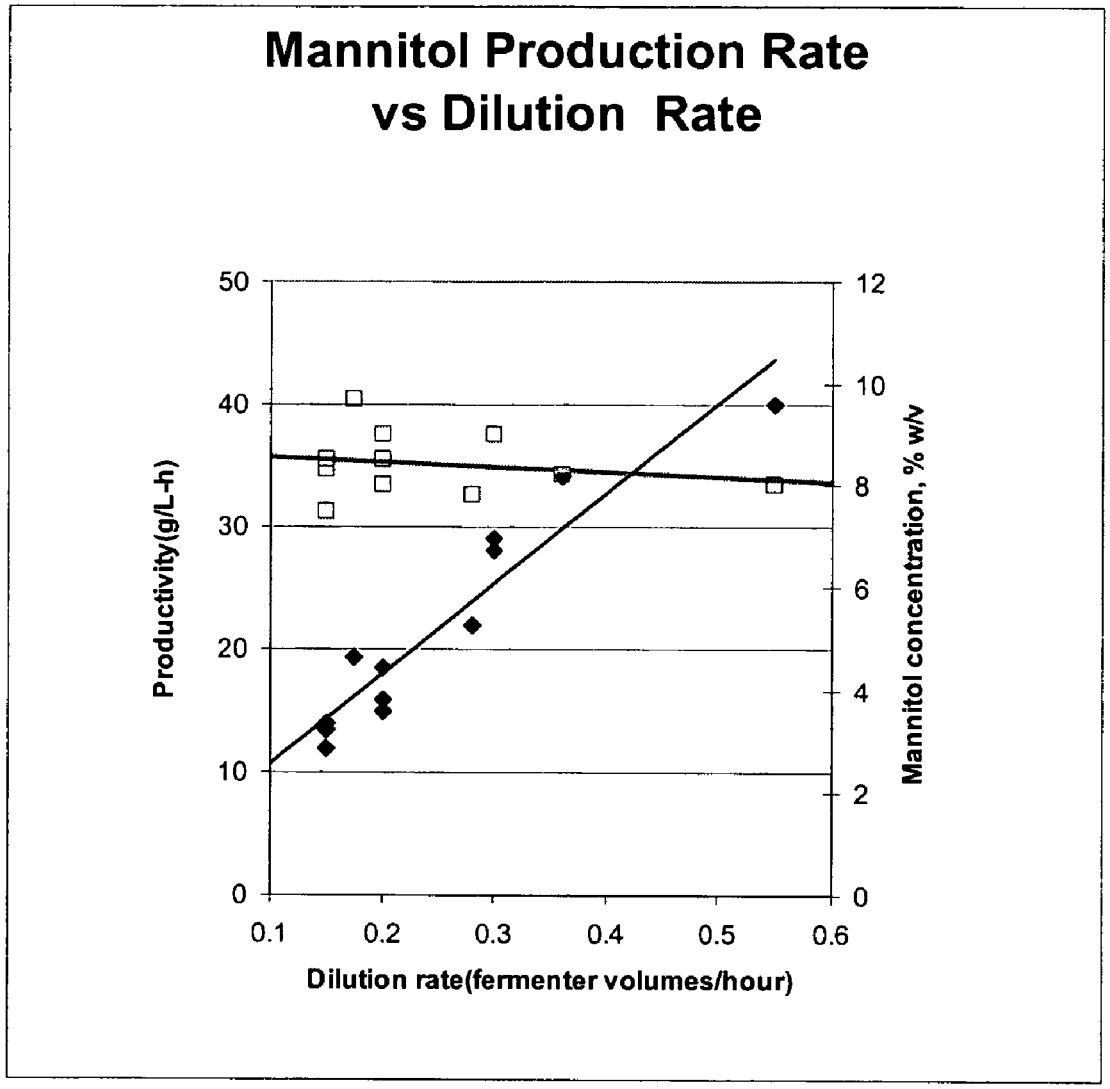
FIG. 2 shows the effect of dilution rate on volumetric productivity and mannitol concentration in cell recycle fermentations. Open squares, mannitol concentration. Closed diamonds, volumetric productivity.
Figure 3:
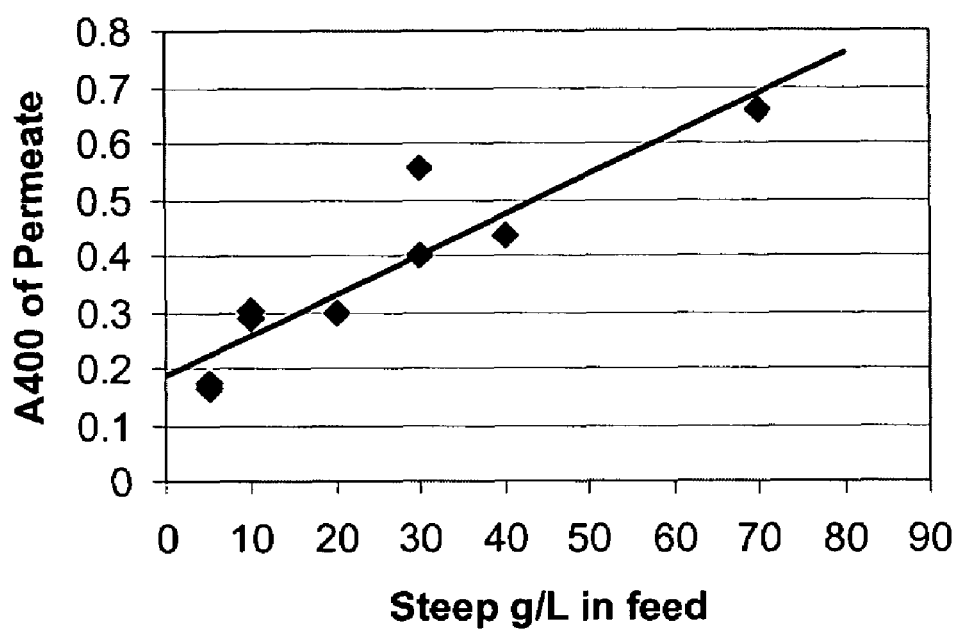
FIG. 3 shows permeate color at various steep concentrations in cell recycle fermentations.

Seed flasks were grown as described in example 6. Fermenters with a 1 L working volume were prepared according to Example 6 except that the initial substrate concentrations were 12% fructose and 6% glucose (added as 200 g of high fructose corn syrup and 54 g of Krystar liquid fructose concentrate). After inoculation with 50 mL of seed, the fermentations were incubated under the conditions described in Example 6. Meanwhile a hollow fiber filter (AGT Model UFP-500-E-4A) was sterilized with 0.2 N NaOH and rinsed with sterile water. After incubation of the fermenters for 14 hours the initial carbohydrate was exhausted and a continuous feed was started. The feed solutions contained about 100 to about 125 g/L fructose, preferably 100 g/L and glucose equal to 50% of the fructose, obtained by mixing the appropriate amounts of HFCS and liquid fructose. The feed solutions also contained manganous sulfate at 0.05 g/L (manganous sulfate can be used at about 0.025 to about 0.20 g/l Mn) and 10-40 g/L corn steep liquor, preferably at 10 g/L. Feed was added to the fermenter at various rates as indicated in FIG. 1. At the same time, broth from the fermenters was pumped through the hollow fiber filter at 0.5 liter per minute and returned to the fermenter. The inlet pressure on the filter was maintained in the 4-7 phi range. Permeate flow was controlled by a pump on the permeate outlet. Permeate was removed at the same rate as the addition of feed plus base in order to keep a constant volume. At the end of the initial 14 hour batch fermentation stage the mannitol concentration was typically 10-11%, while fructose and glucose were each 0-2%. After the recycle was started, the mannitol concentration typically was maintained at 8-10%. A series of fermentations were run at various substrate concentrations, dilution rates and corn steep concentrations. Each fermentation was run for 48-96 hours. The results are shown in FIGS. 1 and 2. The biggest factor in determining the productivity was the dilution rate. Productivities increased from 10 to 40 g/L-h over a dilution range of 0.1-0.5 vol/h. The cell concentrations reached more than 60 optical density units at 660 nm. The final concentration of mannitol in these experiments was less than that of the batch process, typical of a recycle process, ranging from about 8-10%, and did not vary significantly with dilution rate.

It is desirable in a manufacturing process for a crystalline product like mannitol to minimize the amount of organic fermentation nutrients, making recovery and purification easier. Because the nutrients were fed continuously, it was found that the maximum rates in the recycle fermenters could be maintained with only 10 g/L steep and no peptone compared to an optimum of 60 g/L steep and 1 g/L peptone in the fed-batch process. The permeate color, measured as absorbance at 400 nm, was much lower in the recycle process when the steep was reduced to 10 g/L (FIG. 2).

The recycle process gives the producer a choice of a method with higher output per time and volume. The batch method yields higher concentrations. Therefore, the process is very versatile and the producer can choose according to their relative costs of fermentation and evaporation.

Example 8

Use of Calcium Carbonate as a pH Control Agent and Filtering Agent

Calcium carbonate is known as a pH control agent in fermentation. It has the advantage that it can be added to the fermenter before sterilization and does not require automatic pH control equipment. Also, it can be converted to $CaSO_4$ by addition of sulfuric acid and as such can act as a filter aid for clarification of the product. Therefore, tests were conducted to determine the effectiveness of different concentrations of $CaCO_3$ for pH control and their effect on mannitol production. Seeds and 2-liter fermenters were prepared in the same way as example 14 except the inoculum for each fermenter was 100 mL from the seed fleaker, the steep addition was 62.5 g, no peptone was added and calcium carbonate (Hubercarb Q6) was added at the indicated concentrations before sterilization. Protease (0.6 mL per fermenter of GC106) was added prior to inoculation. No pH control was applied to tests 1-5. The following conditions were tested:

| | |
|---|---|
| 1 | 0 g/l $CaCO_3$ |
| 2 | 22.5 g/L $CaCO_3$ |
| 3 | 45 g/L $CaCO_3$ |
| 4 | 67.5 g/L $CaCO_3$ |
| 5 | 90 g/L $CaCO_3$ |
| 6 | 90 g/L $CaCO_3$, with NaOH control |
| 7 | Control, no $CaCO_3$, with NaOH control |

Figure 4:
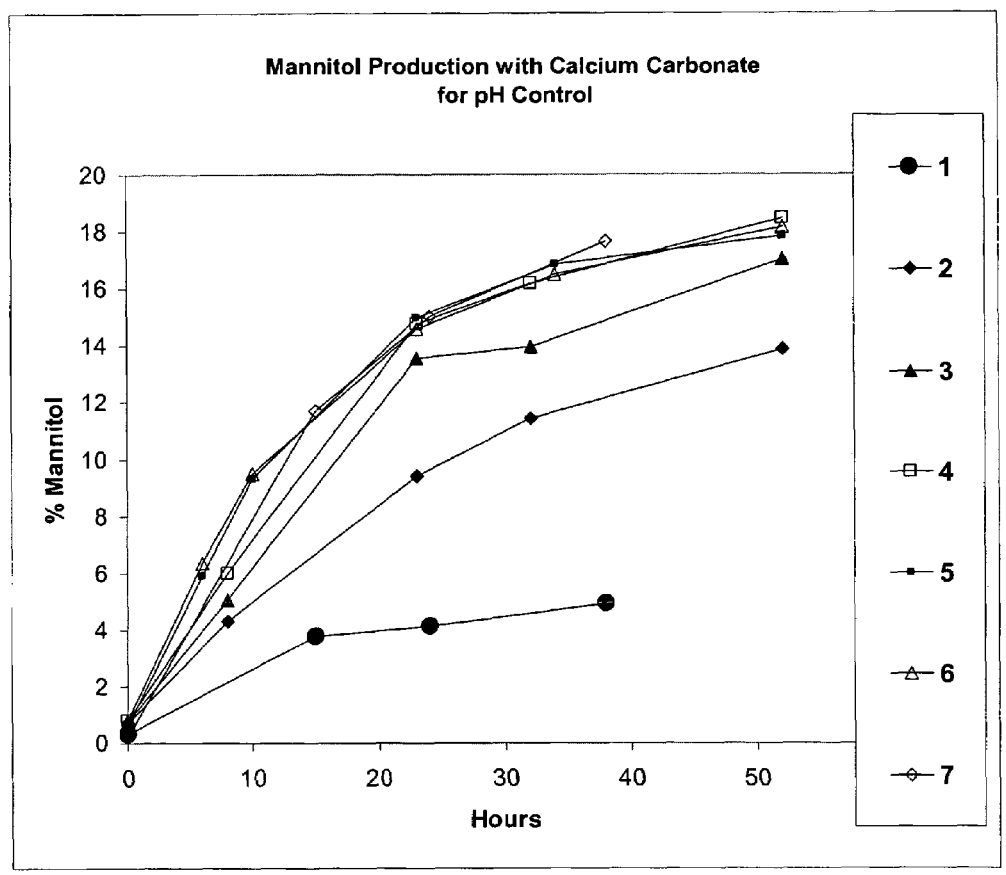
FIG. 4 shows the use of calcium carbonate as a pH control agent. 1, 0 g/l $CaCO_3$; 2, 22.5 g/L $CaCO_3$; 3, 45 g/L $CaCO_3$; 4, 67.5 g/L $CaCO_3$; 5, 90 g/L $CaCO_3$; 6, 90 g/L $CaCO_3$, with NaOH control; 7, Control, no $CaCO_3$, with NaOH control.

The results in FIG. 4 clearly showed that $CaCO_3$ at the proper concentration was equivalent to NaOH with respect to mannitol production. Without $CaCO_3$ or NaOH control, the pH fell to 3.5 by 15 hours and mannitol production was very poor (<50 g/L in 40 hours). With increasing $CaCO_3$ concentration the mannitol production increased, until a maximum was reached at 67.5 g/L as no further improvement was seen at 90 g/L. Having pH controlled by using NAOH did not improve the results when 90 g/L $CaCO_3$ was present. High levels of $CaCO_3$ had no negative effect as the level of mannitol produced at 90 g/L $CaCO_3$ was equivalent to that produced with no $CaCO_3$ and NaOH control.

To test the whether conversion of the $CaCO_3$ to $CaSO_4$ could generate an effective filter medium, broth (1 L) from test 5, 90 g $CaCO_3$ was treated with concentrated sulfuric acid to adjust the pH down from 5 to 2.3. Overhead stirring was used for mixing and the acid (37 mL) was added dropwise over 30 minutes. There was vigorous foaming as $CO_2$ was released between pH 3.5 and 2.8. Once the pH fell to 2.3, foam receded and acid addition was stopped. This slurry of broth and $CaSO_4$ was vacuum filtered on a Buchner funnel with a fine mesh nylon screen. The initial filtrate was cloudy, but as the $CaSO_4$ layer built up on the filter the filtrate gradually cleared. After about 500 mL had passed, the filtrate appeared to be clear of $CaSO_4$ and the initial filtrate was returned to the main body of treated broth, which was continually applied to the filter. The cake of $CaSO_4$ was about ¾ inch thick on the funnel. The filtrate had an absorbance of 0.43 at 660 nm. Typical whole cell broths have absorbances of about 14, although this particular broth could not be measured because of the $CaCO_3$. These results showed that this procedure could be used to remove more than 95% of solids (as A660) from the medium.

Example 9

Multiple Transfers

Many production facilities use fermenter-to-fermenter transfers or drop and add strategies to inoculate fermentations and avoid the need for many seeds. To test whether our process is stable for multiple transfers, successive fleakers were inoculated, using broth from a 24-hour-old fermentation to inoculate the next one (10% transfer). This was done for 5 cycles. Each fermentation was run out to 70-73 hours to test productivity. These were batch runs with 30% fructose. The end result, shown in Table X, was that the fifth run was slightly better than the first. Cycle 3 had a pH control failure for part of the run and produced less than the others, but subsequent runs were at the expected level. Therefore, it should be possible to operate for at least 5 cycles from only one seed fermenter. This confirms the robustness and suitability of this organism for an industrial process. Interestingly, no increase in productivity was seen in adapting the organism to 30% fructose, at least for 5 cycles.

TABLE X

Multiple transfers

| Cycle number | Hours | Mannitol, g/L |
|---|---|---|
| 1 | 70 | 182 |
| 2 | 73 | 195 |
| 3 | 71 | 156* |
| 4 | 73 | 198 |
| 5 | 73 | 196 |

*Note:
Cycle 3 had a 23 hour pH control failure (pH fell to 4.0).

Example 10

Cell Separation by Centrifugation

The lactobacillus cells can be easily removed by centrifugation. The supernatant obtained in this manner is clear and can yield a high purity mannitol as illustrated in the following examples. A fermentation broth produced by the method in example 6 was subjected to centrifugation at 11,000 rpm, 5-6° C., 20 min). The clear supernatant was further treated with charcoal (Nuchar SA-20) at concentrations of 0.5 or 1% g/vol for 0.5-2 hours with stirring. Treatment temperatures of 75° C. or 23 to 37° C. were also compared. The charcoal was removed by vacuum filtration over a Whatman number 42 filter. During this procedure there was no measurable loss of mannitol.

To ease filtration, diatomaceous earth (DE, Eagle Picher FW14) can be used as a filter aid; however testing showed that this was not necessary in most cases. DE (0.5-1% g/vol) was also occasionally applied with charcoal while stirring to ease the following filtration step. However, the addition of DE in any step led to the loss of some mannitol.

Centrifugation and charcoal treatment as described yielded a clear and colorless product. The absorbance at 405 nm was only 0.7-0.8 after centrifugation and was further reduced to 0.2(0.5% charcoal) or 0.1(1% charcoal).

One drawback of the hot charcoal treatment method was a visible caramelization of the broth under temperature, therefore care was taken not to overheat the broth. With ambient temperature charcoal there is no caramelization effect, but the clarification process is complicated by charcoal particle sizes that are too fine. We found that a temperature of about 75±3° C. was the most desirable.

Example 11

Cell Separation by Vacuum Filtration

The fermentation broth was also effectively clarified by vacuum filtration. Filtration was tested using a Buchner funnel at lab scale. A medium porosity DE was used as filter aid cake. Filtration attempts were performed under ambient and 70°-80° C. temperature. Elevated temperature caused denaturation of the organic particles and favored the filtration process.

By adjusting conditions, the best clarification of the fermentation broth using filtration was achieved when the broth was mixed with charcoal (1% g/vol) and DE (0.5% g/vol), heated up to 75-80° C., kept for 30 min, and filtered on a Buchner funnel with DE filter aid cake. The filtrate was clear, and the filtration ran fast. Addition of anti-foaming agents will also likely aid the process.

Example 12

Cell Separation by Hollow Fiber Filtration

We tested the use of hollow fiber microfiltration to clarify the fermentation broth. Cells were separated with a hollow fiber unit with a 500,000 Dalton molecular weight cut-off (Amersham Biosciences, Hollow Fiber Cartridge, Model number UFP-500-E-9A). The filter was operated at 20 psi inlet pressure and 6 liters per minute recycle rate. In a typical example, 30 liters of fermentation broth was reduced to 0.5 liter of retentate, which was further diafiltered with 1.5 liter of water and again reduced to 1 liter volume. In this way, more than 98% of the mannitol in the broth was recovered in the permeate. Cell density at the end of fermentation was measured by absorbance at 660 nm and ranged from 14-16 O.D. units. After the hollow fiber treatment, this was reduced to 0.03-0.05 O.D. units. In one version of the process an ultrafiltration step using a filter with a 10,000 Da molecular weight cut-off was used either instead of, or in addition to, charcoal treatment to remove all the molecules larger than 10 kDa. This ultrafiltration step was run in a similar manner as the microfiltration, except with an AGT UFP 10-C-9A filter.

The purest product was obtained by carrying out the microfiltration, ultrafiltration, and a charcoal treatment with polish filtration. Depending on the final product purity needs however, the microfiltration can be sufficient prior to crystallization.

Example 13

Batch Evaporation

Batch evaporation was conducted in a 5 gallon Pfaudler reactor under 24 inches of mercury at 35-59 C (best is 53-58° C.) or a Buchi rotary evaporator at 34-38 C. Several examples are given in Table XI

TABLE XI

Batch evaporation of clarified fermentation broth

| Initial volume | Final volume | Concentration factor | Bath temp. ° C. | Time, hr | Equipment design |
|---|---|---|---|---|---|
| 13.75 L | 7.0 L | 1.96 | 52.5-58.3 | 2.5 hours | 5 gal Pfaudler reactor |
| 10.0 L | 4.0 L | 2.5 | 35.0-59.5 | 2.0 hours | 5 gal Pfaudler reactor |
| 4.1 L | 2.1 L | 1.95 | 34-38 | ~7 hours | Classical distillation |

Vacuum was 24-26 inches of Hg in all cases

There are some potential drawbacks with this procedure. First, the entire volume under concentration is exposed to elevated temperature for extended times which can lead to caramelization of the organic components, including the product itself. This can increase the viscosity and color intensity and can result in a more complicated crystallization of mannitol from the solution. This problem will be compounded if the mother-liquor is recycled to recover the uncrystallized mannitol. Second, some foaming occurs during the process. This can potentially be controlled with different antifoam agents. Care needs to be taken when using batch evaporation to reduce the exposure time and temperature of the mannitol solution.

Example 14

Continuous Flow Evaporation

A series of experiments were performed to check thin-layer (rolling-film, continuous flow) evaporation and optimize it. In this case we tested evaporation in a rolling-film evaporator (UIC, model RD-4) at various temperatures, using filtrate that had been clarified by microfiltration, ultrafiltration and charcoal treatment.

This continuous flow system included a jacketed heating column with rolling bars inside, a feeding column, a concentrated broth receiver, a cold jacketed column with a distillate collector, and a dry-ice column with a condensate receiver. The chiller maintained the condenser jacket temperature between −12° C. and +12° C. Vacuum was in the range of 13-32 torr.

This approach has two major advantages. First, it limits the amount of caramelization since the time of exposure to the high temperature is very short (between 30 sec. and 2-3 min depending on scale) in comparison to several hours using batch evaporation. Second, this procedure practically excludes any foaming.

A number of operating conditions were tested. The rotation speed of the rollers in the heating column was set to maintain about 184-185 rpm. Higher rotation rates produced a film which was too thin and caused drying out instead of concentration. Lower rates decreased the extent of concentration. We varied the feeding rate from about 8 ml/min up to about 40 ml/min and found that an optimum level of about 33-35 ml/min. The temperature range between 53.5° C. up to 95.0° C. was tested, with the optimal temperature about 94.0-94.5° C. The vacuum applied varied from 13.5 torr up to 32.9 torr, and was usually held at about 24.0-27.0.

Data on the concentration of hot charcoal treated broth is given in Table XII. The temperature optimum of about 95° C. worked best in our experiment. Lower temperatures may be better, but not below about 40-45° C., since it is possible product will precipitate from the concentrated broth. A higher vacuum could also increase the extent of the concentration.

TABLE XII

Continuous Flow Evaporation

| | Volume Processed, L | Volume Collected L | Vacuum torr | Temperature ° C. | Rate of Feeding, ml/min | Chiller Temp ° C. | Total Time |
|---|---|---|---|---|---|---|---|
| Test 1 | 3.0 | 2.3 | 27.7-32.9 | 53.5-82.4 | 8-36 | 0-+8 | 3 h 10 min |
| Test 2 | 10.0 | 7.75 | 13.5-24.6 | 80.9-94.5 | 33-40 | −12-+12 | 7 h 40 min |
| Test 3 | 10.0 | 7.0 | 26.8-31.0 | 94.4-95.0 | 27-38 | −2-+10 | 3 h 10 min |

Example 15

Crystallization

The general procedure is as follows. Concentrated broth is transferred to a temperature controlled vessel while the broth is hot (at least above 40° C.) and moderate stirring is applied immediately (~3 RPM). If the concentrated broth has cooled to below 40° C., it should be reheated, making sure that all precipitated mannitol is redissolved. If crystallization is performed in the same reactor as evaporation, the heat is then removed and the mixture is stirred. Next, the temperature of the solution is decreased to approximately 22-23° C. as slowly as possible, but no faster than 1 degree per minute, providing a smooth gradual decrease. For example, the transition from 40-45° C. to 22-23° C. can take 2-3 hours or more. The slower the cooling process, the fewer centers of crystallization that emerge simultaneously resulting in larger mannitol crystals that separate more cleanly from the mother liquor and washes.

With a 32-34% mannitol content, the first crystals should appear between about 34-37° C. In the case of over-concentration, the crystallization starts at a temperature higher than about 38-40° C. and by the time the slurry reaches about 22-23° C. it is too thick to stir which will make the further processing difficult.

For the same reason, transferring the concentrated warm broth into a cold crystallization kettle should be avoided to avoid abrupt change of the temperature. It is useful to have the kettle preheated to the temperature of the broth, otherwise crystals will have the tendency to grow on the inside walls of the kettle and complicate the process of transferring them into the separator.

Example 16

Mannitol Crystal Separation by Centrifugation

In one example, a Broadbent basket centrifuge with a 4 L basket (23 cm diameter) operated at 1200-1500 rpm was successfully used to collect and wash the crystals. Two washes (1-1.5 liters of ice-cold water per kg mannitol) resulted in crystals that contained no detectable impurities (Table XIV). The wash was applied as a spray while the rotor was running.

Example 17

Mannitol Crystal Separation by Vacuum Filtration

To test vacuum filtration, we used a Buchner ceramic funnel with double-folded cheese cloth as the filter. An ice-cold water wash was applied a few minutes after the filtration started (as soon as mother-liquor is removed from the surface layer of the crystals and they are still moist. The cold temperature prevents dissolution of the crystals. The wash is applied until its filtrate is clear, using a water volume of between 1/10-1/5 of the of the original slurry volume. When using vacuum filtration, cold wash water is evenly spread on the top of the filter cake.

Example 18

Mannitol Recovery

Figure 6:
FIG. 6 shows a diagram of mannitol recovery.
Figure 6:
Figure 6:
Figure 6:
Figure 6:
Figure 6:

The following example illustrates the preferred recovery process as applied to 28 liters of fermentation broth, according to the scheme in FIG. 6. The results are summarized in Table XIII. Cells were separated from the fermentation broth by the microfiltration procedure described in Example 12. This step removed more than 99.7% of the cells as measured by optical density at 660 nm. The permeate was further purified by ultrafiltration through a 10 kDa MWCO hollow fiber filter operated in the same manner as the microfilter. More than 99% of the mannitol remained in the permeate at this stage.

The filtrate was next treated hot with charcoal to remove low molecular weight impurities. The filtrate was heated to 75° C. over 10 min with stirring. The heat was then turned off and the broth was retained under this temperature for 5 min with stirring. Charcoal (Nectar SA-20, 150 g) was added over 2 min with efficient agitation. The charcoal treatment was continued over a 2.5 hour period, allowing the temperature to drop to 65° C. after 30 minutes, and 41° C. after the full 2.5 hours. A final polish filtration was then performed to remove the charcoal. This was carried out using a plate and frame pressure filter (Serfilco, 1777 Shermer Road, Northbrook, Ill., Model 02-7PPMH) with Micronics style 114 filter cloth under a pressure of 60 psi. Only 2% of the mannitol was lost in the charcoal treatment and filtration and this could probably be recovered by rinsing the charcoal, which was not done in this case.

The charcoal treated product was then concentrated by evaporation in a 5 gal Pfaudler batch reactor. Approximately 12.5 liter was loaded at a time and evaporated at 53-58° C. and 24 inches of Hg vacuum for 2 hours resulting in 6.3 liters of concentrate. This was repeated on the second half of the batch resulting in another 6.95 liters of concentrate.

The concentrate was then cooled to induce crystallization following the procedures in Example 15. It was gradually cooled to 3-6° C. with gentle stirring and held overnight at that temperature before harvesting the crystals.

Removal of the crystals from the mother liquor was done in this case with a basket centrifuge as described in example 16. The crystals received two washes with ice-cold water to remove any traces of residual fructose, glucose, acetic acid or lactic acid. About half of the mannitol from the starting fermenter broth was present in this crop of crystals. Of the remainder, most was in the supernatants from the basket centrifugation and could be re-concentrated or combined with another batch for further processing and recovery. Therefore, less than 4% of the starting material was not recovered. Of the starting impurities (glucose, fructose, lactic acid, acetic acid), more than 90% of them were in the first supernatant and the remainder was removed to below the level of detection by the washes.

Finally, the crystals dried easily at 50-55° C. under 25-28 inches of Hg vacuum in less than 24 hours to less than 0.1% moisture.

TABLE XIII

Composition of recovery fractions

| Operation | Vol. L | Mannitol Conc % w/v | Total g | % of Initial | Fructose Conc % w/v | Total g | % of Initial | Glucose Conc % w/v | Total g | % of Initial | Lactic acid Conc % w/v | Total g | % of Initial | Acetic acid Conc % w/v | Total g | % of Initial |
|---|---|---|---|---|---|---|---|---|---|---|---|---|---|---|---|---|
| Fermenter | 28.0 | 13.4 | 3755 | 100.0 | 3.8 | 1070 | 100.0 | 3.4 | 946 | 100.0 | 3.3 | 918 | 100.0 | 2.0 | 554 | 100.0 |
| Hollow fiber 500k permeate | 28.6 | 13.4 | 3827 | 101.9 | 3.7 | 1072 | 100.3 | 3.4 | 968 | 102.3 | 3.6 | 1021 | 111.2 | 2.3 | 644 | 116.1 |
| Hollow fiber 500k retentate | 0.8 | 3.3 | 27 | 0.7 | 0.8 | 7 | 0.6 | 0.7 | 6 | 0.6 | 0.8 | 6 | 0.7 | 0.6 | 4 | 0.8 |
| Hollow fiber 10k permeate | 27.6 | 13.5 | 3722 | 99.1 | 4.3 | 1188 | 111.1 | 3.4 | 929 | 98.2 | 3.5 | 960 | 104.6 | 2.3 | 638 | 115.0 |
| Hollow fiber 10k retentate | 0.5 | 6.3 | 32 | 0.8 | 1.6 | 8 | 0.7 | 1.5 | 8 | 0.8 | 1.7 | 8 | 0.9 | 1.1 | 5 | 1.0 |
| Charcoal + Filter Press | 27.1 | 13.4 | 3632 | 96.7 | 3.7 | 1007 | 94.1 | 3.2 | 879 | 92.9 | 3.3 | 903 | 98.4 | 2.1 | 572 | 103.2 |
| Evaporation + | Crystal | 92.7 | | | 0.6 | | | 0.8 | | | bd | | | bd | | |

TABLE XIII-continued

Composition of recovery fractions

| | | Mannitol | | | Fructose | | | Glucose | | | Lactic acid | | | Acetic acid | | |
|---|---|---|---|---|---|---|---|---|---|---|---|---|---|---|---|---|
| | | | Total | | | Total | | | Total | | | Total | | | Total | |
| Operation | Vol. L | Conc % w/v | g | % of Initial | Conc % w/v | g | % of Initial | Conc % w/v | g | % of Initial | Conc % w/v | g | % of Initial | Conc % w/v | g | % of Initial |
| Crystallization + Basket centrifuge | cake, wet | | | | | | | | | | | | | | | |
| M-L Super.[1] | 11.2 | 8.9 | 993 | 26.5 | 9.2 | 1035 | 96.8 | 8.3 | 927 | 98.0 | 8.1 | 908 | 98.9 | 4.6 | 517 | 93.3 |
| Wash super.[1-2] | 4.1 | 10.8 | 445 | 11.9 | 1.5 | 62 | 5.8 | 1.3 | 54 | 5.7 | 1.7 | 68 | 7.4 | 0.8 | 34 | 6.1 |
| Wash super.[2-3] | 3.0 | 11.5 | 339 | 9.0 | 0.2 | 5 | 0.5 | 0.1 | 3 | 0.3 | 0.3 | 8 | 0.8 | 0.1 | 2 | 0.4 |
| Dried crystals | | 104.2 | 1711 | 45.6 | bd[4] | bd | bd | bd | bd | bd | bd | bd | bd | bd | bd | bd |
| All fractions | | | | 94.5 | | | 104.5 | | | 105.4 | | | 108.8 | | | 101.6 |

[1]M-L Super.: Supernatant from centrifugation of concentrated cooled mother liquor.
[2]Wash 1 -super: Supernatant from centrifugation of first wash of crystals
[3]Wash 2 -super: Supernatant from centrifugation of second wash of crystals
[4]bd: Below level of detection. Level of detection was <0.03%

We claim:

1. An improved process for continuous fed-batch fermentative production of mannitol, the process comprising culturing a microorganism capable of producing mannitol in a fermentation broth under conditions suitable to produce mannitol, the improvement comprising a fermentation broth having corn steep liquor as a complex nitrogen source and about 0.2 ml/L to about 1 ml/L protease.

2. The improved process of claim 1, wherein the fermentation broth comprises about 0.01 g/L to about 0.2 g/L tryptophan.

3. The improved process of claim 1, wherein the fermentation broth comprises about 0.5 g/L to about 20 g/L casein hydrolysate.

4. The improved process of claim 1, wherein the fermentation broth comprises about 0.5 g/L to about 20 g/L casein hydrolysate and about 0.01 g/L and about 0.2 g/L tryptophan.

5. The improved process of claim 1, wherein the fermentation broth comprises about 0.01 g/L to about 0.2 g/L tryptophan, about 0.01 g/L to about 0.2 g/L tyrosine, and about 0.01 g/L to about 0.2 g/L aspartic acid.

6. The improved process of claim 1, wherein the pH of the fermentation broth is about 5.0 to about 6.0 during fermentation.

7. The improved process of claim 1, wherein production of mannitol is greater than about 150 g/L.

8. The improved process of claim 1, wherein the rate of production of mannitol is greater than about 6 g/L-h.

9. The improved process of claim 1, wherein the microorganism is *Lactobacillus intermedius, Leuconostoc mesenteroides* subsp. *dextranicum, Lactobacillus cellobiosus, Leuconostoc paramesenteroides, Lactobacillus fermentum, Lactobacillus buchneri, Leuconostoc amelibiosum, Lactobacillus brevis, Lactobacillus citrovorum* or a combination thereof.

10. The improved process of claim 1, wherein the pH during the continuous fed-batch fermentative production is controlled with $NH_4OH$, NaOH, gaseous $NH_3$, $CaCO_3$, or a combination thereof.

11. The improved process of claim 1, wherein the process further comprises clearing the fermentation broth by centrifugation, filtration or hollow fiber filtration.

12. The improved process of claim 1, wherein the process further comprises clearing the fermentation both by filtration, wherein the filtration comprises adding $CaCO_3$ to the fermentation broth and lowering the pH with sulfuric acid and filtering the fermentation broth.

13. The improved process of claim 1, wherein the process further comprises concentrating the fermentation broth to about 30% to 36% mannitol by batch evaporation or continuous flow evaporation.

14. The improved process of claim 13, wherein the process further comprises crystallizing the concentrated fermentation broth.

15. The improved process of claim 1, wherein the fermentation broth comprises about 64 g/L initial volume to about 120 g/L initial volume of corn steep liquor.

16. An improved process for continuous recycle fermentative production of mannitol, the process comprising culturing a microorganism capable of producing mannitol in a fermentation broth under conditions suitable to produce mannitol, the improvement comprising using fermentation broth having corn steep liquor as a complex nitrogen source and about 0.2 ml/L to about 1 ml/L protease.

17. The improved process of claim 16, wherein the fermentation broth comprises about 0.01 g/L to about 0.2 g/L tryptophan.

18. The improved process of claim 16, wherein the fermentation broth comprises about 0.5 g/L to about 20 g/L casein hydrolysate.

19. The improved process of claim 16, wherein the fermentation broth comprises about 0.5 g/L to about 20 g/L casein hydrolysate and about 0.01 g/L and about 0.2 g/L tryptophan.

20. The improved process of claim 16, wherein the fermentation broth comprises about 0.01 g/L to about 0.2 g/L tryptophan, about 0.01 g/L to about 0.2 g/L tyrosine, and about 0.01 g/L to about 0.2 g/L aspartic acid.

21. The improved process of claim 16, wherein the pH of the fermentation broth is about 5.0 to about 6.0 during fermentation.

22. The improved process of claim 16, wherein a dilution range is about 0.1 to about 0.55 vol/h.

23. The improved process of claim 16, wherein the rate of production of mannitol is greater than about 30 g/L-h.

24. The improved process of claim 16, wherein the microorganism is *Lactobacillus intermedius, Leuconostoc mesenteroides* subsp. *dextranicum, Lactobacillus cellobiosus, Leuconostoc paramesenteroides, Lactobacillus fermentum, Lactobacillus buchneri, Leuconostoc amelibiosum, Lactobacillus brevis, Lactobacillus citrovorum* or a combination thereof.

25. The improved process of claim 16, wherein the pH during the continuous fed-batch fermentative production is controlled with $NH_4OH$, NaGH, gaseous $NH_3$, $CaCO_3$, or a combination thereof.

26. The improved process of claim 16, wherein the process further comprises clearing the fermentation broth by centrifugation, filtration or hollow fiber filtration.

27. The improved process of claim 16, wherein the process further comprises clearing the fermentation broth by filtration, wherein the filtration comprises adding $CaCO_3$ to the fermentation broth and lowering the pH with sulfuric acid and filtering the fermentation broth.

28. The improved process of claim 16, when the process further comprises concentrating the fermentation broth to about 30% to 36% mannitol by batch evaporation or continuous flow evaporation.

29. The improved process of claim 28, wherein the process further comprises crystallizing the concentrated fermentation broth.

30. The improved process of claim 16, wherein the fermentation broth comprises about 9% to about 15% fructose and from about 2% to about 10% glucose.

31. The improved process of claim 16, wherein the fermentation broth comprises about 10 to about 40 g/L corn steep liquor.

* * * * *